(12) United States Patent
Bach et al.

(10) Patent No.: US 6,451,839 B1
(45) Date of Patent: Sep. 17, 2002

(54) INDOLE SPLA$_2$ INHIBITORS

(75) Inventors: Nicholas James Bach, Indianapolis; Robert Delane Dillard, Zionsville; Susan Elizabeth Draheim, Indianapolis; Edward David Mihelich, Carmel; Tulio Suarez, Greenwood, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/762,069

(22) PCT Filed: Aug. 2, 1999

(86) PCT No.: PCT/US99/17459

§ 371 (c)(1),
(2), (4) Date: Jan. 30, 2001

(87) PCT Pub. No.: WO00/07590

PCT Pub. Date: Feb. 17, 2000

Related U.S. Application Data

(60) Provisional application No. 60/095,114, filed on Aug. 3, 1998.

(51) Int. Cl.$^7$ .................. A61K 31/404; C07D 209/40
(52) U.S. Cl. ................. 514/415; 514/419; 548/483; 548/507
(58) Field of Search .................. 548/483, 507; 514/415, 419

(56) References Cited

U.S. PATENT DOCUMENTS

| | | | |
|---|---|---|---|
| 5,312,928 A | 5/1994 | Goldin et al. | 548/495 |
| 5,578,634 A | 11/1996 | Bach et al. | 514/419 |
| 5,604,254 A | 2/1997 | Quadro | 514/419 |
| 5,654,326 A | 8/1997 | Bach et al. | 514/419 |
| 5,684,034 A | 11/1997 | Bach et al. | 514/38 |
| 5,767,139 A | 6/1998 | Maw et al. | 514/419 |
| 6,252,084 B1 * | 6/2001 | Bach et al. | 548/113 |

* cited by examiner

Primary Examiner—Fiona T. Powers
(74) Attorney, Agent, or Firm—Roger S. Benjamin

(57) ABSTRACT

A class of novel indole is disclosed together with the use of such compounds for inhibiting sPLA$_2$ mediated release of fatty acids for treatment of inflammatory diseases such as septic shock.

23 Claims, No Drawings

INDOLE SPLA₂ INHIBITORS

This application claims the benefit of U.S. provisional application No. 60/095,114, filed Aug. 3, 1998.

FIELD OF THE INVENTION

This invention relates to novel indole compounds useful for inflammatory diseases.

BACKGROUND OF THE INVENTION

The structure and physical properties of human non-pancreatic secretory phospholipase $A_2$ (hereinafter called, "sPLA₂") has been thoroughly described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

Indole type sPLA₂ inhibitors having gyloxylamide, acetamide and hydrazide substituents are described in U.S. Pat. Nos. 5,654,326; 5,684,034; and 5,578,634 respectively.

It is believed that sPLA₂ is a rate limiting enzyme in the arachidonic acid cascade which hydrolyzes membrane phospholipids. Thus, it is important to develop compounds which inhibit sPLA₂ mediated release of fatty acids (e.g., arachidonic acid). Such compounds would be of value in general treatment of conditions induced and/or maintained by overproduction of sPLA₂; such as sepsis or rheumatoid arthritis.

It is desirable to develop new compounds and treatments for sPLA₂ induced diseases.

SUMMARY OF THE INVENTION

This invention is a novel indole compound to inhibit mammalian sPLA₂ mediated release of fatty acids.

This invention is also a novel class of indole having potent and selective effectiveness as inhibitors of mammalian sPLA₂.

This invention is also a indole compound in the treatment of Inflammatory Diseases.

This invention is also a pharmaceutical composition containing the indole of the invention.

This invention is also a method of preventing and treating Inflammatory Diseases in mammals by administration of a therapeutically effective amount of the indole of the invention.

This invention is also the indole compounds of the invention or compositions comprising the compounds of the invention as active ingredient for use as a medicament in the treatment of Inflammatory Diseases.

Definitions

The term, "Inflammatory Diseases" refers to diseases such as inflammatory bowel disease, sepsis, septic shock, adult respiratory distress syndrome, pancreatitis, trauma-induced shock, asthma, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA₂ mediated release of fatty acid and to thereby inhibit or prevent the arachidonic acid cascade and its deleterious products.

The term, "indole nucleus" refers to a nucleus (having numbered positions) with the structural formula (X):

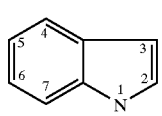

(X)

The indole compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo. The term, heterocyclic radical, refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo(1,2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, spiro[5.5]undecanyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (a):

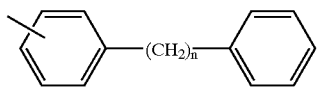

(a)

where n is a number from 1 to 8.

The term, "non-interfering substituent", refers to radicals suitable for substitution at positions 4,5,6 and/or 7 of the indole nucleus and on other nucleus substituents (as hereinafter described for Formula I), and radicals suitable for substitution on the heterocyclic radical and carbocyclic radical as defined above. Illustrative non-interfering radicals are $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_8$ alkylsulfinyl, $C_1$–$C_8$ alkylsulfonyl, $C_2$–$C_8$ haloalkoxy, $C_1$–$C_8$ haloalkylsulfonyl, $C_2$–$C_8$ haloalkyl, $C_1$–$C_8$ hydroxyalkyl, —C(O)O($C_1$–$C_8$ alkyl), —($CH_2$)$_n$—O—($C_1$–$C_8$ alkyl), benzyloxy, phenoxy, phenylthio, —(CONHSO$_2$R), —CHO, amino, amidino, bromo, carbamyl, carboxyl, carbalkoxy, —($CH_2$)$_n$—$CO_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where R is $C_1$–$C_8$ alkyl and n is from 1 to 8.

The term, "organic substituent" refers to a monovalent radical consisting of carbon and hydrogen with or without oxygen, nitrogen, sulfur, halogen, or other elements. Illustrative organic substituents are $C_1$–$C_8$ alkyl, aryl, $C_7$–$C_{14}$ aralkyl, $C_7$–$C_{14}$ alkaryl, $C_3$–$C_8$ cycloalkyl, $C_1$–$C_8$ alkoxyalkyl and these groups substitued with halogen, —CF$_3$, —OH, $C_1$–$C_8$ alkyl, amino, carbonyl, and —CN.

The term, "acylsulfonamide group" is an (acidic group) represented by the formula:

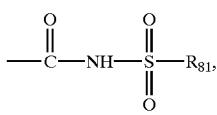

where $R_{81}$ is an organic substituent or the radical —CF$_3$.

The term, "(acidic group)" means an organic group which when attached to an indole nucleus, through suitable linking atoms (hereinafter defined as the "acid linker"), acts as a proton donor capable of hydrogen bonding. Illustrative of an (acidic group) are the following:

-5-tetrazolyl,

—SO$_3$H,

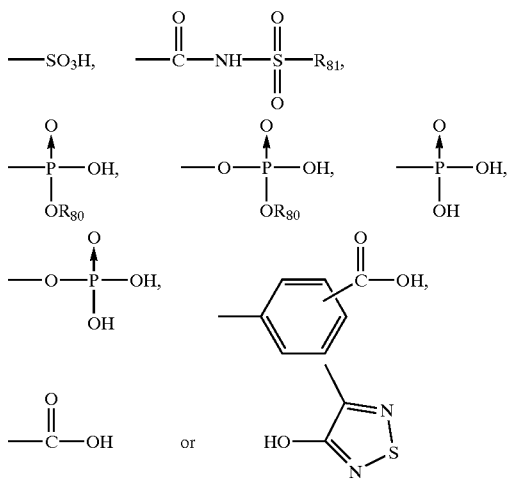

where n is 1 to 8, $R_{80}$ is a metal or $C_1$–$C_8$ and $R_{81}$ is an organic substituent or —CF$_3$.

The words, "acid linker" refer to a divalent linking group symbolized as, —(La)—, which has the function of joining the 4 or 5 position of the indole nucleus to an acidic group in the general relationship:

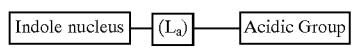

The words, "acid linker length", refer to the number of atoms (excluding hydrogen) in the shortest chain of the linking group —($L_a$)— that connects the 4 or 5 position of the indole nucleus with the acidic group. The presence of a carbocyclic ring in —($L_a$)— counts as the number of atoms approximately equivalent to the calculated diameter of the carbocyclic ring. Thus, a benzene or cyclohexane ring in the acid linker counts as 2 atoms in calculating the length of —($L_a$)—. Illustrative acid linker groups are;

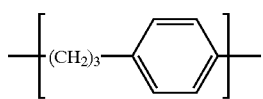

(a)

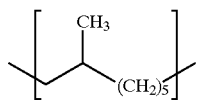

(b)

-continued (c)

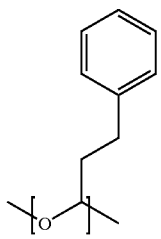

wherein, groups (a), (b), and (c) have acid linker lengths of 5, 7, and 2, respectively.

The term, "amine", includes primary, secondary and tertiary amines.

The terms, "mammal" and "mammalian" include human.

The term, "alkylene chain of 1 or 2 carbon atoms" refers to the divalent radicals, —CH$_2$—CH$_2$— and —CH$_2$—.

The term, "group containing 1 to 4 non-hydrogen atoms" refers to relatively small groups which form substituents at the 2 position of the indole nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —CF$_3$, —Cl, —Br, —NO$_2$, —CN, —SO$_3$; and (ii) groups having hydrogen atoms which contain less than 4 non-hydrogen atoms such as —CH$_3$, —C$_2$H$_5$, and —CH=CH$_2$.

The term "ureido" means the radical, —NH—C(O)—NH$_2$.

The term "thioureido" means the radical —NH—C(S)—NH$_2$.

The term "spiro[5.5]undecanyl" refers to the group represented by the formula;

The indole Compounds of the Invention:

The compounds of the invention have the general formula (I) or a pharmaceutically acceptable salt, solvate or prodrug thereof;

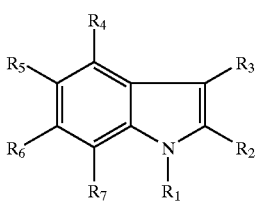

(I)

wherein;

R$_1$ is selected from groups (a), (b) and (c) wherein;
(a) is C$_7$–C$_{20}$ alkyl, C$_7$–C$_{20}$ haloalkyl, C$_7$–C$_{20}$ alkenyl, C$_7$–C$_{20}$ alkynyl, carbocyclic radical, or heterocyclic radical, or
(b) is a member of (a) substituted with one or more independently selected non-interfering substituents; or
(c) is the group —(L$_1$)—R$_{11}$; where, —(L$_1$)— is a divalent linking group of 1 to 8 atoms and where R$_{11}$ is a group selected from (a) or (b);

R$_2$ is hydrogen, or a group containing 1 to 4 non-hydrogen atoms plus any required hydrogen atoms;

R$_3$ is —(L$_3$)—Z, where —(L$_3$)— is a divalent linker group selected from a bond or a divalent group selected from:

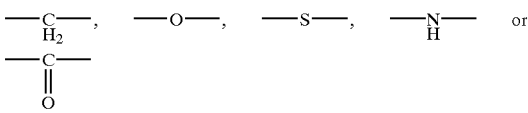

and Z is selected from a group represented by the formulae,

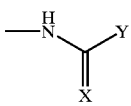

wherein, X is oxygen or sulfur; Y is —NH$_2$, C$_1$–C$_4$ alkyl, —CF$_3$, —CONH$_2$ or —CH$_2$Z where Z is F, Cl, Br, or I;

R$_4$ and R$_5$ are independently selected from hydrogen, a non-interfering substituent, or the group, —(L$_a$)-(acidic group); wherein —(L$_a$)—, is an acid linker having an acid linker length of 1 to 8, provided, that at least one of R$_4$ and R$_5$ must be the group, —(L$_a$)— (acidic group);

R$_6$ and R$_7$ are selected from hydrogen, non-interfering substituent, carbocyclic radical, carbocyclic radical substituted with non-interfering substituent(s), heterocyclic radicals, and heterocyclic radical substituted with non-interfering substituent(s).

Preferred Subgroups of Compounds of Formula (I)

I. Preferred R$_1$ Substituents

A preferred subclass of compounds of formula (I) wherein for R$_1$ the divalent linking group —(L$_1$)— are those corresponding to the formulae (VIIa), (VIIb), (VIIc), (VIId), (VIIe), and (VIIf):

 (VIIa)

 (VIIb)

 (VIIc)

 (VIId)

 (VIIe)

 (VIIf)

where Q$_1$ is a bond or any of the divalent groups (VIIa), (VIIb), (VIIc), (VIId), (VIIe), and (VIIf) and each R$_{10}$ is independently hydrogen, C$_{1-8}$ alkyl, C$_{1-8}$ haloalkyl or C$_{1-8}$ alkoxy.

Particularly preferred as the linking group —(L$_1$)— of R$_1$ is a divalent alkylene chain of 1 or 2 carbon atoms, namely, —(CH$_2$)— or —(CH$_2$—CH$_2$)—.

The preferred group for R$_{11}$ is a substituted or unsubstituted group selected from the group consisting of C$_5$–C$_{14}$ cycloalkyl, $C_5$–$C_{14}$ cycloalkenyl, phenyl, naphthyl, norbornanyl, bicycloheptadienyl, tolulyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (a);

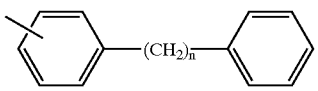

(a)

where n is a number from 1 to 8.

Particularly preferred are compounds wherein for $R_1$ the combined group —($L_1$)—$R_{11}$ is selected from the group consisting of

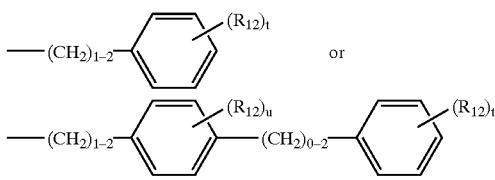

where $R_{12}$ is a radical independently selected from halo, $C_1$–$C_8$ alkyl, $C_1$–$C_8$ alkoxy, —S—($C_1$–$C_8$ alkyl), —O—($C_1$–$C_8$ alkyl) and $C_1$–$C_8$ haloalkyl where t is a number from 0 to 5 and u is a number from 0 to 4.

II. Preferred $R_2$ Substituents $R_2$ is preferably selected from the group consisting of hydrogen, $C_1$–$C_4$ alkyl, $C_2$–$C_4$ alkenyl, —O—($C_1$–$C_3$ alkyl), —S—($C_1$–$C_3$ alkyl), —$C_3$–$C_4$ cycloalkyl —$CF_3$, halo, —$NO_2$, —CN, —$SO_3$. Particularly preferred $R_2$ groups are selected from hydrogen, methyl, ethyl, propyl, isopropyl, cyclopropyl, —F, —$CF_3$, —Cl, —Br, or —O—$CH_3$.

III. Preferred $R_3$ Substituents

A preferred subclass of compounds of formula (I) are those wherein X is oxygen.

Another preferred subclass of compounds of formula (I) are those wherein Z is a ureido group.

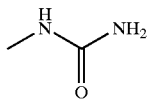

Most preferred are compounds of formula (I) wherein $R_3$ is the ureido group. For the group $R_3$ it is preferred that the linking group —($L_3$)— be a bond.

IV. Preferred $R_4$ Substituents

Another preferred subclass of compounds of formula (I) are those wherein $R_4$ is a substituent having an acid linker with an acid linker length of 2 or 3 and the acid linker group, —($L_4$)—, for $R_4$ is selected from a group represented by the formula;

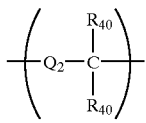

where $Q_2$ is selected from the group —($CH_2$)—, —O—, —NH—, —C(O)—, and —S—, and each $R_{40}$ is independently selected from hydrogen, $C_1$–$C_8$ alkyl, aryl, $C_1$–$C_8$ alkaryl, $C_1$–$C_8$ alkoxy, aralkyl, and halo. Most preferred are compounds where the acid linker, —($L_4$)—, for $R_4$ is selected from the specific groups;

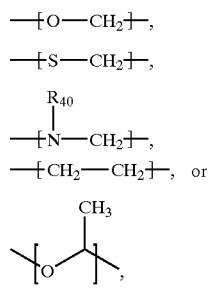

where $R_{40}$ is hydrogen or $C_1$–$C_8$ alkyl. Preferred as the (acidic group) in the group $R_4$ are acidic groups selected from:

-5-tetrazolyl,

—$SO_3H$,

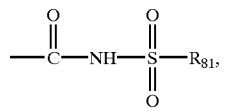

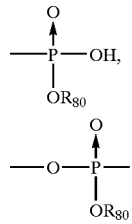

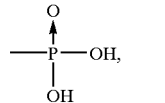

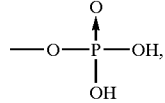

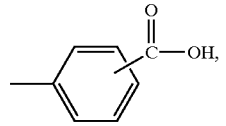

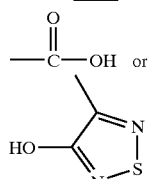

where $R_{80}$ is a metal or $C_1$–$C_8$ and $R_{81}$ is an organic substituent or —$CF_3$. A salt or a prodrug derivatives of the (acidic group) is also a suitable substituent.

Particularly preferred are acidic groups selected from:
—$CO_2H$,
—$SO_3H$,
—$P(O)(OH)_2$ or salt, and prodrug (e.g., ester, amide) derivatives thereof.

V. Preferred $R_5$ Substituents

The most preferred acidic group in the compounds of the invention is a carboxylic acid group, —$CO_2H$. Preferred acid linker, —$(L_a)$—, for $R_5$ is selected from of;

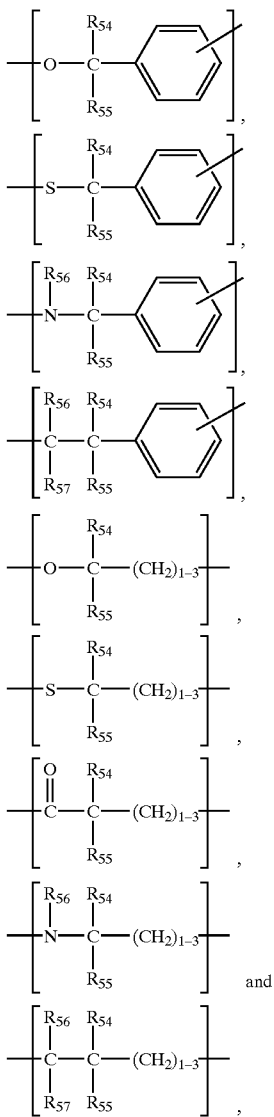

wherein $R_{54}$, $R_{55}$, $R_{56}$ and $R_{57}$ are each independently hydrogen, $C_1$–$C_8$ alkyl, $C_1$–$C_8$ haloalkyl, aryl, $C_1$–$C_8$ alkoxy, or halo.

VI. Preferred (Acidic Group) for $R_4$ and/or $R_5$ Substitutions

At least one of $R_4$ and $R_5$ must be the group, —$(L_a)$-(acidic group). The preferred (acidic group) on the group —$(L_a)$-(acidic group) of $R_4$ or $R_5$ is selected from —$CO_2H$, —$SO_3H$, or —$P(O)(OH)_2$. In addition, it is preferred that only one $R_4$ or $R_5$ substituents be the group, —$(L_a)$-(acidic group). Most preferred is that the $R_4$ substituent be the group, —$(L_a)$-(acidic group). The most preferred (acidic group) is carboxyl.

V. Preferred $R_6$ Substituents

Another preferred subclass of compounds of formula (I) are those wherein for $R_6$ the non-interfering substituent is methyl, ethyl, propyl, isopropyl, thiomethyl, —O-methyl, $C_4$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —$C(O)O(C_1$–$C_6$ alkyl), —$(CH_2)_n$—$O$—$(C_1$–$C_6$ alkyl), benzyloxy, phenoxy, phenylthio, —$(CONHSO_2R)$, —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and carbonyl; where R is $C_1$–$C_8$ alkyl and n is from 1 to 8.

Preferred compounds of the invention are those having the general formula (II), or a pharmaceutically acceptable salt, solvate or prodrug derivative thereof;

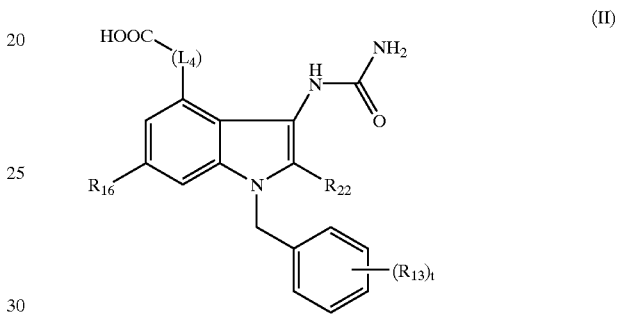

(II)

wherein;

$R_{22}$ is selected from hydrogen, methyl, ethyl, propyl, isopropyl, cyclopropyl, —F, —$CF_3$, —Cl, —Br, or —O—$CH_3$;

—$(L_4)$— is a divalent group selected from;

—$[O$—$CH_2]$—,

—$[S$—$CH_2]$—, $$-\left[\begin{array}{c}R_{40}\\|\\N-CH_2\end{array}\right]-,$$

$$-\left[\begin{array}{cc}R_{40} & R_{41}\\|&|\\C-C\\|&|\\R_{42}&R_{43}\end{array}\right]-,$$

or

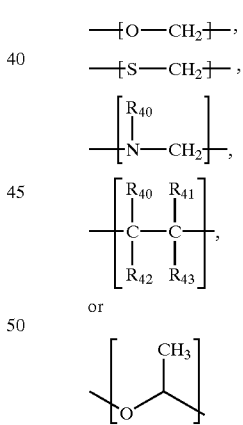

where $R_{40}$, $R_{41}$, $R_{42}$, and $R_{43}$ are each independently selected from hydrogen or $C_1$–$C_8$ alkyl.

$R_{16}$ is selected from hydrogen, $C_1$–$C_8$ alkyl, $C_1$–$C_8$ alkoxy, $C_1$–$C_8$ alkylthio $C_1$–$C_8$ haloalkyl, $C_1$–$C_8$ hydroxyalkyl, and halo.

$R_{13}$ is selected from hydrogen and $C_1$–$C_8$ alkyl, $C_1$–$C_8$ alkoxy, —S—$(C_1$–$C_8$ alkyl), $C_1$–$C_8$ haloalkyl, $C_1$–$C_8$, phenyl, halophenyl, hydroxyalkyl, and halo, and t is an integer from 0 to 5.

A preferred compound (and all pharmaceutically acceptable salts, solvates and prodrug derivatives thereof) which is illustrative of the compounds of the invention is as follows:

Compound C1

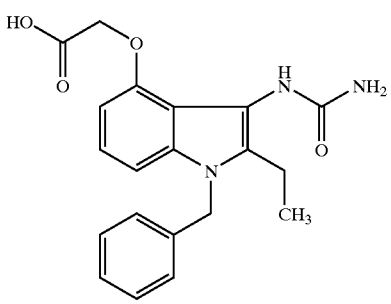

(C1)

The salts of the above indole compounds represented by formulae (I) and (II) are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin. For example, the (acidic group) of the substituent $R_4$ of Formula I may be selected as —$CO_2H$ and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of diastereomers and diastereomers, because they have different melting points, different boiling points, and different solubilities can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-Chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula (I) (in a medium such as dimethylformamide) 4-(2-chloroethyl) morpholine hydrochloride (available from Aldrich Chemical Co., Milwaukee, Wis. USA, Item No. C4,220-3).

Method of Making the Compounds of the Invention

The synthesis of the indole compounds of the invention (viz., Compounds of Formulae I and II) can be accomplished by well known methods as recorded in the chemical literature. In particular, the indole starting materials may be prepared by the synthesis schemes taught in U.S. Pat. No. 5,654,326; the disclosure of which is incorporated herein by reference. Procedures useful for the synthesis of the starting material are shown in the Scheme below:

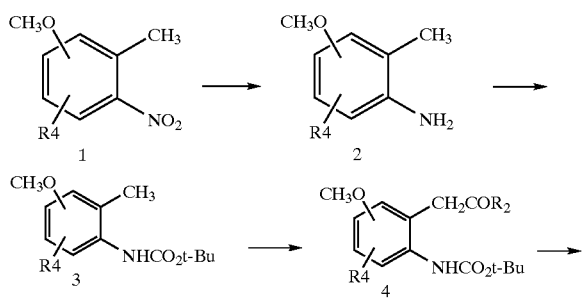

To obtain the 3-ureido-1H-indole compounds (and other substituted compounds) substituted in the 4-position with an (acidic group) linked through an oxygen atom, the reactions outlined in the scheme supra, are used (for conversions 1 through 5, see ref. Robin D. Clark, Joseph M. Muchowski, Lawrence E. Fisher, Lee A. Flippin, David B. Repke, Michel Souchet, *Synthesis,* 1991, 871–878, the disclosures of which are incorporated herein by reference). The starting material ortho-nitrotoluene, 1, is readily reduced to 2-methyl,3-metoxyaniline, 2. Reduction of 1 is by the catalytic hydrogenation of the corresponding nitrotoluene using palladium on carbon as catalyst. The reduction can be carried out in ethanol or tetrahydrofuran (THF) or a combination of both, using a low pressure of hydrogen. The aniline, 2, obtained, is converted to the N-tert-butyloxycarbonyl derivative, 3, in good yield, on heating with di-tert-butyl dicarbonate in THF at reflux temperature. The dilithium salt of the dianion of 3 is generated at −40 to −20° C. in THF using sec-butyllithium and reacted with the appropriately substituted N-methoxy-N-methylalkanamide to form the ketone 4. This product (4) may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature. (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, *Adv. Drug Res.,* 1977, 12, 176, the disclosure of which is incorporated herein by reference). The 4-hydroxyindole, 7, is alkylated with an alpha bromoalkanoic acid ester in dimethylformamide (DMF) using sodium hydride as a base, with reactions conditions similar to that described for the conversion of 5 to 6. The α-((indol-4-yl)oxy)alkanoic acid ester, 8, is reacted with bis(2,2,2-trichloroethyl)azodicarboxylate in diethylether to give adduct 9. The adduct 9, was dissolved in tetrahydrofuran and reacted with zinc and glacial acetic acid, followed by treatment with excess trimethylsilylisocyanate to give the urea compound 10. This product, 10, is hydrolyzed using 1N sodium hydroxide in methanol. The final 3-ureido-indole compound, 11, is isolated either as the free carboxylic acid or as its sodium salt or in both forms.

Alternatively, other electrophiles may be substituted for trimethylsilylisocyanate to provide intermediates useful for conversion to novel inhibitors. These other electrophiles include, but are not limited to, acid anhydrides, ethyl oxalyl chloride, and ethoxycarbonylisothiocyanate. These agents react with the 3-aminoindole that results from the reduction of compound 9 as described above using zinc and acetic acid.

Compounds substituted at the 5 position of the indole nucleus with an (acidic group) may be prepared by methods and starting materials shown in schemes 2 and 3 of U.S. Pat. No. 5,654,326; the disclosure of which is incorporated herein by reference.

The thioureido analogs of the compounds of this invention can be made by substituting ethoxycarbonylisothiocyanate for trimethylsilylisocyanate to produce an intermediate compound which can be hydrolyzed to the thioureido-indole analog of compound 11. The thioureido compounds can also be isolated as the free acid or as its sodium salt.

Methods of Using the Compounds of the Invention

The indole compounds described herein are believed to achieve their beneficial therapeutic action principally by direct inhibition of mammalian (including human) sPLA$_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA$_2$ mediated release of fatty acids comprises contacting mammalian sPLA$_2$ with an therapeutically effective amount of indole compounds corresponding to Formulae (I) or (II) as described herein including salt or a prodrug derivative thereof.

Another aspect of this invention is a method for treating Inflammatory Diseases such as inflammatory bowel disease, septic shock, adult respiratory distress syndrome, panceatitis, trauma, asthma, bronchial asthma, allergic rhinitis, rheumatoid arthritis, osteoarthritis, and related diseases which comprises administering to a mammal (including a human) a therapeutically effective dose of the indole compound of the invention (see, formula I and II).

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention (per Formulae I or II) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the indole compound of the invention together with a pharmaceutically acceptable carrier or diluent therefor. The present pharmaceutical formulations are prepared by known procedures using well known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 thru 8 are illustrative only and are not intended to limit the scope of the invention in any way. "Active ingredient", refers to a compound according to Formula (I) or (II) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

| | Quantity (mg/tablet) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

| | Weight |
|---|---|
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active ingredient, are made as follows:

| | |
|---|---|
| Active ingredient | 225 mg |
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

All of the products of the Examples described below as well as intermediates used in the following procedures showed satisfactory nmr and ir spectra. They also had the correct mass spectral values.

EXAMPLE 1

Preparation of [[2-Ethyl-1-(phenylmethyl)-3-ureido-1H-indol-4-yl]oxy]acetic acid, a compound represented by the formula

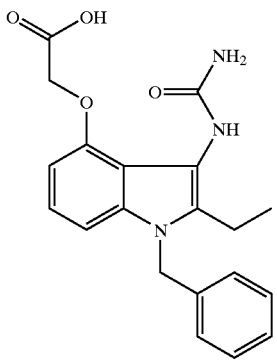

Part A. Preparation of 2-Ethyl-4-methoxy-1H-indole

A solution of 140 mL (0.18 mol) of 1.3M sec-butyl lithium in cyclohexane was added slowly to N-tert-butoxycarbonyl-3-methoxy-2-methylaniline (21.3 g, 0.09 mol) in 250 mL of THF keeping the temperature below −40° C. with a dry ice-ethanol bath. The bath was removed and the temperature allowed to rise to 0° C. and then the bath replaced. After the temperature has cooled to −60° C., 18.5 g (0.18 mol) of N-methoxy-N-methylpropanamide in an equal volume of THF was added dropwise. The reaction mixture was stirred 5 minutes, the cooling bath removed and stirring continued an additional 18 hours. It was then poured into a mixture of 300 mL of ether and 400 mL of 0.5N HCl. The organic layer was separated, washed with water, brine, dried over $MgSO_4$, and concentrated at reduced pressure to give 25.5 g of crude 1-[2-(tert-butoxycarbonylamino)-6-methoxyphenyl]-2-butanone. This material was dissolved in 250 mL of methylene chloride and 50 mL of trifluoroacetic acid and stirred for a total of 17 hours. The mixture was concentrated at reduced pressure and ethyl acetate and water added to the remaining oil. The ethyl acetate was separated, washed with brine, dried ($MgSO_4$) and concentrated. The residue was chromatographed three times on silica eluting with 20% EtOAc/hexane to give 13.9. g of 2-ethyl-4-methoxy-1H-indole.

Analyses for $C_{11}H_{13}NO$:

| Calculated: | C, 75.40; | H, 7.48; | N, 7.99 |
|---|---|---|---|
| Found: | C, 74.41; | H, 7.64; | N, 7.97. |

Part B. Preparation of 2-Ethyl-4-methoxy-1-(phenylmethyl)-1H-indole

2-Ethyl-4-methoxy-1H-indole (4.2 g, 24 mmol) was dissolved in 30 mL of DMF and 960 mg (24 mmol) of 60% NaH/mineral oil was added. After 1.5 hours, 2.9 mL (24 mmol) of benzyl bromide was added. After 4 hours, the mixture was diluted with water and extracted twice with ethyl acetate. The combined ethyl acetate extracts were washed with brine, dried ($MgSO_4$) and concentrated at reduced pressure. The residue was chromatographed on silica gel eluting with 20% EtOAc/hexane to give 3.1 g (49% yield) of 2-ethyl-4-methoxy-1-(phenylmethyl)-1H-indole.

Part C. Preparation of 2-Ethyl-4-hydroxy-1-(phenylmethyl)-1H-indole.

A solution of 3.1 g (11.7 mmol) of 2-ethyl-4-methoxy-1-(phenylmethyl)-1H-indole and 48.6 mL of 1M $BBr_3/CH_2Cl_2$ in 50 mL of methylene chloride was stirred at room temperature for 5 hours and concentrated at reduced pressure. The residue was dissolved in ethyl acetate, washed with brine and dried ($MgSO_4$). After concentrating at reduced pressure, the residue was chromatographed on silica gel eluting with 20% EtOAc/hexane to give 1.58 g (54% yield) of 2-ethyl-4-hydroxy-1-(phenylmethyl)-1H-indole, mp, 86–90° C.

Analyses for $C_{17}H_{17}NO$:

| Calculated: | C, 81.24; | H, 6.82; | N, 5.57 |
|---|---|---|---|
| Found: | C, 81.08; | H, 6.92; | N, 5.41. |

Part D. Preparation of [[2-Ethyl-1-(phenylmethyl)-1H-indol-4-yl]oxy]acetic acid tert-butyl ester 2-Ethyl-4-hydroxy-1-(phenylmethyl)-1H-indole (5.82 g, 20 mmol) was added to 7.82 g (24 mmol) cesium carbonate in 25 mL DMF and the mixture stirred at 35° C. for 30 minutes. After cooling to 20° C., a solution of tert-butyl bromoacetate (4.65 g, 23.8 mmol) in 5 mL DMF was added and stirring maintained until the reaction was judged complete by TLC analysis (several hours). The mixture was diluted with water and extracted with ethyl acetate. The ethyl acetate solution was washed with brine, dried ($MgSO_4$) and concentrated at reduced pressure to give 6.8 g of solid. Mass spectrum: 365

Analyses for $C_{23}H_{27}NO_3$:

| Calculated: | C, 75.59; | H, 7.75; | N, 3.83 |
|---|---|---|---|
| Found: | C, 75.87; | H, 7.48; | N, 3.94. |

Part E. Preparation of [[2-Ethyl-1-(phenylmethyl)-3-ureido-1H-indol-4-yl]oxy]acetic acid tert-butyl ester A solution of 2.3 g (6.3 mmol) [[2-ethyl-1-(phenylmethyl)-1H-indol-4-yl]oxy]acetic acid tert-butyl ester and 4.8 g (12.6 mmol) bis(2,2,2-trichloroethyl) azodicarboxylate in diethyl ether was stirred for 24 hours at room temperature. The resulting solid was filtered and vacuum dried. This adduct (1 g, 1.3 mmol) was dissolved in 10 mL of THF and treated with zinc (1 g) and glacial acetic acid (0.5 mL). After stirring for 30 minutes at room temperature an excess of trimethylsilylisocyanate in 1 mL of THF was added stirring was continued at room temperature for 18 hours. The mixture was diluted with water and extracted with ethyl acetate. The organic layer was washed with brine, dried over $MgSO_4$ and concentrated to dryness to give 0.385 g (69% yield) of the subtitled material. Mass spectrum: 423.

Analyses for $C_{24}H_{29}N_3O_4$:

| Calculated: | C, 68.07; | H, 6.90; | N, 9.92 |
|---|---|---|---|
| Found: | C, 67.92; | H, 6.84; | N, 9.70. |

Part F. Preparation of [[2-Ethyl-1-(phenylmethyl)-3-ureido-1H-indol-4-yl]oxy]acetic acid A solution of [[2-ethyl-1-(phenylmethyl)-3-ureido-1H-indol-4-yl]oxy]acetic acid tert-butyl ester (0.2 g) and trifluoroacetic acid (0.3 mL) in 5 mL of methylene chloride was stirred at room temperature for 18 hours. After concentrating to dryness, the resulting solid was slurried in ether, filtered and air dried to give 0.08 g of titled compound. Mass spectrum: 368.

Exact mass spectral data for $C_{20}H_{21}N_3O_4$:

| | |
|---|---|
| Calculated: | 368.1610 |
| Found: | 368.1613 |

EXAMPLE 2

Preparation of [[3-Acetamido-2-ethyl-1-(phenylmethyl)-1H-indol-4-yl]oxy]acetic acid

[[3-Acetamido-2-ethyl-1-(phenylmethyl)-1H-indol-4-yl]oxy]acetic acid tert-butyl ester (50 mg), obtained according to the procedure specified for Example 1, part E, using acetic anhydride in place of trimethylsilylisocyanate to acylate the crude amine, was stirred in 10 mL of a mixture of 7:1 methanol/tetrahydrofuran and 0.5 mL of a 2 N sodium hydroxide at room temperature overnight, concentrated, and acidified with 1 N hydrochloric acid. The resulting solid was isolated by filtration and vacuum dried.

Exact mass spectral data for $C_{21}H_{23}N_2O_4$: Calculated: 367.1658. Found: 367.1663

EXAMPLE 3

Preparation of [[3-trifluoroacetamido-2-ethyl-1-(phenylmethyl)-1H-indol-4-yl]oxy]acetic acid.

[[3-Trifluoroacetamido-2-ethyl-1-(phenylmethyl)-1H-indol-4-yl]oxy]acetic acid tert-butyl ester (500 mg), obtained according to the procedure specified for Example 1, part E, using trifluoroacetic anhydride in place of trimethylsilylisocyanate to acylate the crude amine, was treated with trifluoroacetic acid (0.5 mL) in 5 mL of dichloromethane at room temperature. After several hours, the reaction was concentrated under vacuum, diluted with water, filtered, and vacuum dried. Mass spectrum: 420

Elemental analysis:

| | | | |
|---|---|---|---|
| Found: | C 62.04 | H 5.12 | N 6.78 |
| Calculated: | C 60.00 | H 4.56 | N 6.66 |

EXAMPLE 4

Preparation of [[3-(Bromo)acetamido-2-ethyl-1-(phenylmethyl)-1H-indol-4-yl]oxy]acetic acid

[[3-(Bromo)acetamido-2-ethyl-1-(phenylmethyl)-1H-indol-4-yl]oxy]acetic acid tert-butyl ester (400 mg), obtained according to the procedure specified for Example 1, part E, using bromoacetic anhydride in place of trimethylsilylisocyanate to acylate the crude amine, was treated with trifluoroacetic acid (1 mL) in 10 mL of dichloromethane at room temperature. After several hours, the reaction was concentrated under vacuum, diluted with water, filtered, and vacuum dried to provide 150 mg of solid. Mass spectrum: 445

Elemental analysis:

| | | | |
|---|---|---|---|
| Found: | C 56.39 | H 4.61 | N 6.1 |
| Calculated: | C 56.64 | H 4.75 | N 6.29 |

EXAMPLE 5

Preparation of [[2-Ethyl-1-(phenylmethyl)-3-thioureido-1H-indol-4-yl]oxy]acetic acid

[[2-Ethyl-1-(phenylmethyl)-3-thioureido-1H-indol-4-yl]oxy]acetic acid tert-butly ester (200 mg), obtained in the same way as example 1, part E, but using ethoxycarbonylisothiocyanate as the electrophile, was dissolved in 8 mL of a mixture of 7:1 methanol/tetrahydrofuran and 1 mL of 2 N sodium hydroxide, stirred at room temperature over night, concentrated to dryness and acidified. The solid was filtered and vacuum dried to provide 90 mg of solid.

Elemental analysis:

| | | | |
|---|---|---|---|
| Found: | C 62.07 | H 5.42 | N 10.94 |
| Calculated: | C 62.64 | H 5.52 | N 10.96 |

EXAMPLE 6

Preparation of [[2-ethyl-3-oxamide-1-(phenylmethyl)-1H-indol-4-yl]oxy]acetic acid

Part A. Preparation of [[2-ethyl-3-oxamide-1-(phenylmethyl)-1H-indol-4-yl]oxy]acetic acid tert-butyl ester

[[2-Ethyl-3-(ethyl)oxamate-1-(phenylmethyl)-1H-indol-4-yl]oxy]acetic acid tert-butyl ester was prepared as described in example 1, part E, but using ethyl oxalyl chloride as electrophile in the presence of pyridine. This intermediate was hydrolyzed in 8 mL of a 7:1 methanol/tetrahydrofuran mixture and 1 mL of 2 N sodium hydroxide to afford the corresponding 3-oxamic acid derivative. This oxamic acid derivative was reacted with carbonyl diimidazole in dichloromethane and the resultant product treated with ammonia (gas) to afford the subtitled compound.

Part B. Preparation of [[2-ethyl-3-oxamide-1-(phenylmethyl)-1H-indol-4-yl]oxy]acetic acid

[[2-Ethyl-3-oxamide-1-(phenylmethyl)-1H-indol-4-yl]oxy]acetic acid tert-butyl ester (200 mg) was hydrolyzed in 8 mL of a 7:1 methanol/tetrahydrofuran mixture and one mL of 2 N sodium hydroxide at room temperature overnight. After concentration to dryness, the product was acidified to yield 120 mg of [[2-ethyl-3-oxamide-1-(phenylmethyl)-1H-indol-4-yl]oxy]acetic acid.

Exact mass spectral data for $C_{21}H_{22}N_3O_5$:

| Calculated: | 396.1559 |
|---|---|
| Found: | 396.1552 |

EXAMPLE 7

Preparation of [[2-ethyl-1-(2-phenyl-phenylmethyl)-3-ureido-1H-indol-4-yl]oxy]acetic acid

Part A. Preparation of N-(2-phenyl-phenylmethyl)-phthalimide (2-Phenyl)-phenylmethyl bromide (6 g, 0.0243 mol) and potassium phthalimide (5 g, 0.0270 mol) were mixed together in dimethyl formamide at room temperature, stirred for 60 hrs, diluted with cold water, and the solid isolated by filtration. After washing with water, isopropyl alcohol, and hexane the white solid was vacuum dried to yield 6.9 g of the subtitled compound. Mass spectrum: 313

Part B. Preparation of 2-phenyl-phenylmethyl amine

N-(2-Phenyl-phenylmethyl)-phthalimide (6.5 g) in 25 cc of hydrazine hydrate were stirred at room temperature overnight. Ice water was added and the solid separated by filtration. The filtrate was salted out with brine and extracted with ethyl acetate. The ethyl acetate extract was washed with water, dried over magnesium sulfate, filtered and concentrated to dryness to afford 3 g of subtitled product as an oil.

Part C. Preparation of 2-ethyl-1,5,6,7-tetrahydro-1-(2-phenyl-phenylmethyl)-4H-indol-4-one 2-Phenyl-phenylmethyl amine (3 g, 0.0164 mol) and an equivalent amount of 2-(2-oxobutyl)-1,3-Cyclohexyldione were dissolved in 30 mL of toluene and heated at reflux temperature with a water separator. After several hours, solvent was stripped off and the residue subjected to flash chromatography on silica eluting with 3:1 hexane/ethyl acetate to afford 4.5 g of the subtitled compound as an oil.

Part D. Preparation of 2-ethyl-4-hydroxy-1-(2-phenyl-phenylmethyl)-1H-indole 2-Ethyl-1,5,6,7-tetrahydro-1-(2-phenyl-phenylmethyl)-4H-indol-4-one (2.17 g, 0.0066 mol) dissolved in 10 mL of tetrahydrofuran was added to a slurry of sodium hydride (0.58 g) in 3 mL of tetrahydrofuran and the mixture was stirred for 15 min at room temperature. Methyl benzene sulfinate (1.13 g) was added and the solution stirred overnight. The reaction mixture was poured into water, the pH adjusted to 6 with acetic acid and extracted with toluene. The organic layer was separated, washed with water and brine, dried with sodium sulfate, concentrated, taken up in toluene (80 mL) and heated at reflux for 1.5 h. After cooling, the mixture was concentrated, dissolved in ether (100 mL), washed with saturated sodium bicarbonate solution, dried over sodium sulfate, concentrated and purified by flash chromatography on silica eluting with 10:1 hexane/ethyl acetate to afford 0.85 g of subtitled material.

Part E. Preparation of [[2-ethyl-1-(2-phenyl-phenylmethyl)-1H-indol-4-yl]oxy]acetic acid tert-butyl ester 2-Ethyl-4-hydroxy-1-(2-phenyl-phenylmethyl)-1H-indole (0.8 g, 0.00245 mol) was added to a slurry of cesium carbonate (0.98 g, 0.003 mol) in 15 mL of dimethylformamide, stirred at room temperature for ten minutes and then the t-butyl bromoacetate was added all at once. After stirring at room temperature overnight, the solution was poured into water and extracted in ethyl acetate. The organic layer was washed with water, dried over magnesium sulfate, filtered and concentrated to an oil that crystallized on standing at room temperature. This material was slurried in hexane and filtered to give 0.93 g of subtitled compound as a tan solid.

Part F. Preparation of [[2-ethyl-1-(2-phenyl-phenylmethyl)-3-ureido-1H-indol-4-yl]oxy acetic acid tert-butyl ester

[[2-Ethyl-1-(2-phenyl-phenylmethyl)-1H-indol-4-yl]oxy] acetic acid tert-butyl ester (0.9 g, 0.0021 mol) was stirred with 2.4 g (0.0063 mol) bis(2,2,2-trichloroethyl) azodicarboxylate in 50 mL of ether at room temperature overnight. The reaction mixture was concentrated to dryness and hexane added. After sitting overnight at room temperature, the precipitated solid was isolated by filtration (0.9 g). This adduct (0.5 g) was dissolved in 5 mL tetrahydrofuran and treated with zinc (0.5 g) and glacial acetic acid (5 mL). After two hours at room temperature, the excess zinc was separated by filtration, washed with tetrahydrofuran, and the combined organic layers concentrated to dryness. The resultant oil was dissolved in tetrahydrofuran, treated with a slight excess of trimethylsilylisocyanate and stirred overnight. The reaction mixture was poured into water and extracted in ethyl acetate. The organic layer was washed with water, dried and concentrated to give the subtitled compound as an oil.

Part G. Preparation of [[2-ethyl-1-(2-phenyl-phenylmethyl)-3-ureido-1H-indol-4-yl]oxy]acetic acid

[[2-Ethyl-1-(2-phenyl-phenylmethyl)-3-ureido-1H-indol-4-yl]oxy]acetic acid tert-butyl ester (0.206 g) was treated with 5 mL of a 7:1 mixture of methanol/tetrahydrofuran at room temperature overnight. After concentrating to dryness and adding 1 mL of 1N HCl, stirring was continued at room temperature for an hour. The resulting solid was filtered off and vacuum dried to provide 0.098 g of [[2-ethyl-1-(2-phenyl-phenylmethyl)-3-ureido-1H-indol-4-yl]oxy]acetic acid.

Exact mass spectral data for $C_{26}H_{26}N_3O_4$:

| Calculated: | 444.1923 |
|---|---|
| Found: | 444.1911 |

EXAMPLE 8

Preparation of [[2-ethyl-1-(2-bromo-phenylmethyl)-3-ureido-1H-indol-4-yl]oxy]acetic acid

Part A. Preparation of [[2-ethyl-1-(2-bromo-phenylmethyl)-1H-indol-4-yl]oxy]acetic acid tert-butyl ester 2-Ethyl-1,5,6,7-tetrahydro-1-(2-bromo-phenylmethyl)-4H-indol-4-one (6.64 g), obtained according to Example 7, Part C, using 2-bromobenzyl amine, was dissolved in 20 mL of toluene, treated with potassium methoxide (5.75 g) and a solution of methyl benzene sulfinate in 3 mL of toluene added. After warming the solution to 30 to 40 degrees for 30 minutes, it was allowed to cool to room temperature and kept there for 2 hours. The solution was cooled to 10 degrees, diluted with toluene, water was added and the toluene layer separated. The toluene layer was heated to 80–85 degrees for 3 hours. The toluene was flash evaporated and the residue subject to flash chromatography on silica eluting with 4/1 chloroform/ethyl acetate to provide 4.5 g of phenolic intermediate. This material was dissolved in 25 mL of dimethylformamide and 5 g of cesium carbonate added. The mixture was warmed to 40 degrees for 30 minutes, cooled to room temperature and tert-butyl bromoacetate added in the same solvent. After stirring at room temperature for 3 hours, water was added, and the mixture extracted in ethyl acetate. The organic layer was washed with water, dried, filtered, and concentrated. The subtitled material (4 g) was precipitated from hexane. Mass spectrum: 444

Part B. Preparation of [[2-ethyl-1-(2-bromo-phenylmethyl)-3-ureido-1H-indol-4-yl]oxy]acetic acid tert-butyl ester

[[2-Ethyl-1-(2-bromo-phenylmethyl)-1H-indol-4-yl]oxy]acetic acid tert-butyl ester (1 g) was converted to the subtitled compound (0.7 g) following the procedure from Example 7, Part F. Mass spectrum: 501

Part C. Preparation of [[2-ethyl-1-(2-bromo-phenylmethyl)-3-ureido-1H-indol-4-yl]oxy]acetic acid

[[2-Ethyl-1-(2-bromo-phenylmethyl)-3-ureido-1H-indol-4-yl]oxy]acetic acid tert-butyl ester (0.7 g) was dissolved in 5 mL of dichloromethane and 1 mL of trifluoroacetic acid was added. After stirring for 4 hours the reaction mixture was concentrated to dryness, the residue dissolved in ethyl acetate and extracted with 1 N sodium hydroxide. This solution was acidified and extracted with ethyl acetate, the solvent removed by flash evaporation, and the residue slurried in 1 N hydrochloric acid. The resulting greenish solid was isolated by filtration and vacuum dried. This material was flash chromatographed on silica eluting with 19:1 ethyl acetate/methanol containing 2.5% acetic acid to provide [[2-ethyl-1-(2-bromo-phenylmethyl)-3-ureido-1H-indol-4-yl]oxy]acetic acid.

Exact mass spectral data for $C_{20}H_{21}BrN_3O$:

| Calculated: | 446.0715 |
|---|---|
| Found: | 446.0688 |

EXAMPLE 9

Preparation of [[2-ethyl-1-(2-(4-fluorophenyl)-phenylmethyl)-3-ureido-1H-indol-4-yl]oxy]acetic acid Part A. Preparation of [[2-ethyl-1-(2-(4-fluorophenyl)-phenylmethyl)-1H-indol-4-yl]oxy]acetic acid tert-butyl ester

[[2-Ethyl-1-(2-bromo-phenylmethyl)-1H-indol-4-yl]oxy]acetic acid tert-butyl ester (1.3 g) was combined with 4-fluoro-phenylboronic acid in 20 mL of n-propanol at room temperature. After 30 minutes, the slurry was treated with palladium acetate, triphenylphosphine and 2 mL of 2 M sodium carbonate solution. The mixture was heated at reflux for one hour, cooled to room temperature and diluted with water. After stirring for 1 hour, the mixture was extracted with ethyl acetate, which was washed, dried, filtered, and concentrated to afford 1.1 g of product.

Part B. Preparation of [12-ethyl-1-(2-(4-fluorophenyl)-phenylmethyl)-3-ureido-1H-indol-4-yl]oxy]acetic acid tert-butyl ester

[[2-Ethyl-1-(2-(4-fluorophenyl)-phenylmethyl)-1H-indol-4-yl]oxy]acetic acid tert-butyl ester was converted to the subtitled compound according to the procedure describe in Example 1, part E.

Part C. Preparation of [[2-ethyl-1-(2-(4-fluorophenyl)-phenylmethyl)-3-ureido-1H-indol-4-yl]oxy]acetic acid

[[2-Ethyl-1-(2-(4-fluorophenyl)-phenylmethyl)-3-ureido-1H-indol-4-yl]oxy]acetic acid tert-butyl ester (0.4 g) was treated with 2 mL of trifluoroacetic acid at room temperature. After two hours the excess acid was removed under vacuum, 5 mL of 1N hydrochloric acid added, the mixture extracted with ethyl acetate, which was washed, dried, and concentrated. The residue was treated with 2 mL of 1 N hydrochloric acid and stirred for several hours. The resulting tan solid was isolated by filtration to afford 0.20 g of [[2-ethyl-1-(2-(4-fluorophenyl)-phenylmethyl)-3-ureido-1H-indol-4-yl]oxy]acetic acid. Mass spectrum: 461

Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents
REACTION BUFFER

| CaCl2.2H2O | (1.47 g/L) |
|---|---|
| KCl | (7.455 g/L) | g/L)
(Sigma A-7030, product of Sigma Chemical Co., St. Louis Mo., USA)
TRIS HCl (3.94 g/L)
pH 7.5 (adjust with NaOH)
ENZYME BUFFER
0.05 NaOAc.3H2O, pH 4.5
0.2NaCl
Adjust pH to 4.5 with acetic acid
DTNB—5,5'-dithiobis-2-nitrobenzoic acid
RACEMIC DIHEPTANOYL THIO—PC
 racemic 1,2-bis(heptanoylthio)-1,2-dideoxy-sn-glycero-3-phosphorylcholine
TRITON X-100™ prepare at 6.249 mg/ml in reaction buffer to equal 10 uM.

REACTION MIXTURE

A measured volume of racemic diheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains lmM diheptanoly thio-PC substrate, 0.29 mm Triton X-100™ detergent, and 0.12 mm DTMB in a buffered aqueous solution at pH 7.5.

Assay Procedure

1. Add 0.2 ml reaction mixture to all wells;
2. Add 10 ul test compound (or solvent blank) to appropriate wells, mix 20 seconds;
3. Add 50 nanograms of sPLA$_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, IC$_{50}$ values were determined. Typically, the IC$_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of IC$_{50}$ values. IC$_{50}$ were determined by plotting log concentration versus inhibition values in the range from 10–90% inhibition.

Results of Human Secreted Phospholipase A$_2$ Inhibition Tests

TABLE

| Compound Example No. | Inhibition of human secreted PLA$_2$ IC50 ± mean deviation |
| --- | --- |
| 1 | 0.049 uM |
| 2 | 65 uM |
| 3 | 51 uM |
| 4 | 45 uM |
| 5 | 6.8 uM |
| 6 | 13 uM |
| 7 | 0.021 uM |
| 8 | 0.074 uM |
| 9 | 0.017 uM |

The compounds of the Examples are useful in inhibiting sPLA$_2$.

While the present invention has been illustrated above by certain specific embodiments, it is not intended that these specific examples should limit the scope of the invention as described in the appended claims.

We claim:

1. An indole compound represented by the formula (I), or a pharmaceutically acceptable salt, solvate, or prodrug derivative thereof;

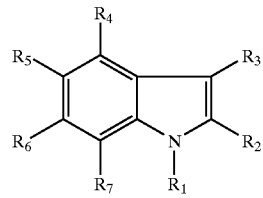

wherein;

R$_1$ is selected from groups (a), (b) and (c) wherein;
(a) is C$_7$–C$_{20}$ alkyl, C$_7$–C$_{20}$ haloalkyl, C$_7$–C$_{20}$ alkenyl, C$_7$–C$_{20}$ alkynyl, carbocyclic radical, or heterocyclic radical, or
(b) is a member of (a) substituted with one or more independently selected non-interfering substituents; or
(c) is the group —(L$_1$)—R$_{11}$; where, —(L$_1$)— is a divalent linking group of 1 to 8 atoms and R$_{11}$ is a group selected from (a) or (b);

R$_2$ is hydrogen, or a group containing 1 to 4 non-hydrogen atoms;

R$_3$ is —(L$_3$)— Z, where —(L$_3$)— is a divalent linker group selected from a bond or a divalent group selected from:

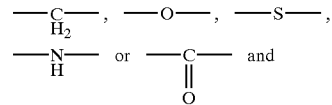

Z is selected from a group represented by the formulae,

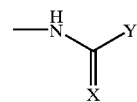

wherein, X is oxygen or sulfur; Y is —NH$_2$, C$_1$–C$_4$ alkyl, —CF$_3$, —CONH$_2$ or —CH$_2$Z where Z is F, Cl, Br, or I;

R$_4$ and R$_5$ each independently selected from hydrogen, a non-interfering substituent, or the group, —(L$_a$)-(acidic group), where —(L$_a$)—, is a divalent acid linker having an acid linker length of 1 to 8; provided that at least one of R$_4$ and R$_5$ must be the group, —(L$_a$)-(acidic group);

R$_6$ and R$_7$ are each independently selected from hydrogen, non-interfering substituent, carbocyclic radical, carbocyclic radical substituted with non-interfering substituent(s), heterocyclic radical, and heterocyclic radical substituted with non-interfering substituent(s).

2. The compound of claim 1 wherein R$_2$ is hydrogen, C$_1$–C$_4$ alkyl, C$_2$–C$_4$ alkenyl, —O—(C$_1$–C$_3$ alkyl), —S—(C$_1$–C$_3$ alkyl), —C$_3$–C$_4$ cycloalkyl —CF$_3$, halo, —NO$_2$, —CN, or —SO$_3$.

3. The compound of claim 1 wherein the acid linker group, —(L$_a$)—, for R$_4$ is selected from a group represented by the formula;

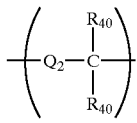

where $Q_2$ is selected from the group —$(CH_2)$—, —O—, —NH—, —C(O)—, and —S—, and each $R_{40}$ is independently selected from hydrogen, $C_1$–$C_8$ alkyl, aryl, $C_1$–$C_8$ alkaryl, $C_1$–$C_8$ alkoxy, aralkyl, and halo.

4. The compound of claim 1 wherein the acid linker, —$(L_a)$—, for $R_5$ is selected from a group represented by the formulae consisting of;

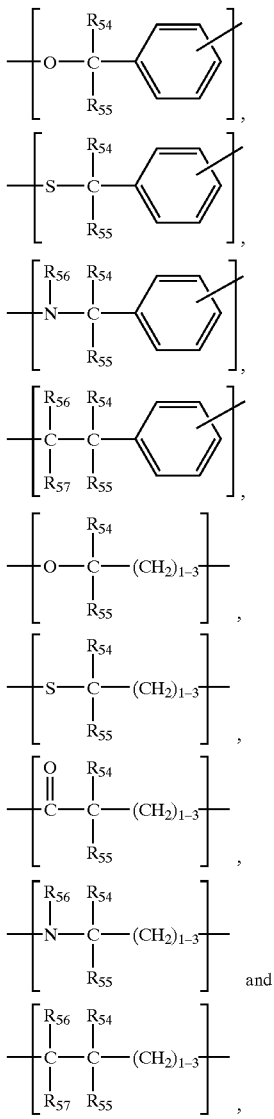

wherein $R_{54}$, $R_{55}$, $R_{56}$ and $R_{57}$ are each independently hydrogen, $C_1$–$C_8$ alkyl, $C_1$–$C_8$ haloalkyl, aryl, $C_1$–$C_8$ alkoxy, or halo.

5. The compound of claim 1 wherein only one of $R_4$ and $R_5$ is the group, —$(L_a)$-(acidic group) and wherein the (acidic group) is selected from the group:

-5-tetrazolyl,

—$SO_3H$,

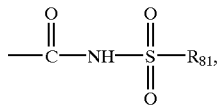

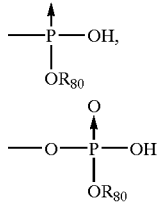

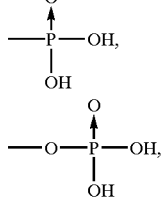

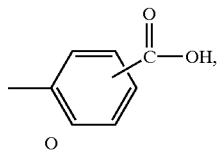

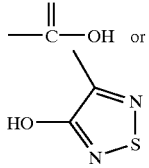

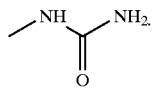

where $R_{80}$ is a metal or $C_1$–$C_8$ alkyl and $R_{81}$ is an organic substituent or —$CF_3$.

6. The compound of claim 5 wherein the (acidic group) is —$CO_2H$.

7. The compound of claim 1 wherein for $R_3$, Z is the group represented by the formula;

and the linking group —$(L_3)$— is a bond.

8. The compound of claim 1 wherein, for $R_6$ the non-interfering substituent is hydrogen, $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_8$ alkylsulfinyl, $C_1$–$C_8$ alkylsulfonyl, $C_2$–$C_8$ haloalkoxy, $C_1$–$C_8$ haloalkylsulfonyl, $C_2$–$C_8$ haloalkyl, $C_1$–$C_8$ hydroxyalkyl, —C(O)O($C_1$–$C_8$ alkyl), —$(CH_2)_n$—O—($C_1$–$C_8$ alkyl), benzyloxy, phenoxy, phenylthio, —(CONHSO_2R), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, or carbonyl; where R is $C_1$–$C_8$ alkyl and n is from 1 to 8.

9. The compound of claim 1 wherein for $R_1$ the divalent linking group —$(L_1)$— is selected from a group represented by the formulae (VIIa), (VIIb), (VIIc), (VIId), (VIIe), and (VIIf):

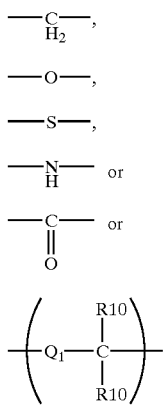

where $Q_1$ is a bond or any of the divalent groups VIIa, VIIb, VIIc, VIId, and VIIe and $R_{10}$ is independently —H, $C_{1-8}$ alkyl, $C_{1-8}$ haloalkyl or $C_{1-8}$ alkoxy.

10. The compound of claim 1 wherein the linking group —($L_1$)— of $R_1$ is —($CH_2$)— or —($CH_2$—$CH_2$)—.

11. The compound of claim 1 wherein for $R_1$ the group $R_{11}$ is a substituted or unsubstituted carbocyclic radical selected from the group consisting of cycloalkyl, cycloalkenyl, phenyl, spiro[5.5]undecanyl, naphthyl, norbornanyl, bicycloheptadienyl, tolulyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (a):

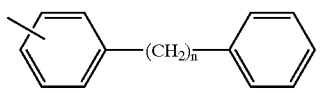

where n is a number from 1 to 8.

12. The compound of claim 11 wherein for $R_1$ the combined group —($L_1$)—$R_{11}$ is selected from the groups;

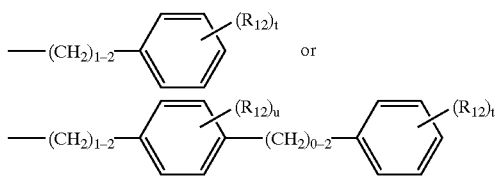

where $R_{12}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl, $C_1$–$C_{10}$ hydroxyalkyl and t is a number from 0 to 5 and u is a number from 0 to 4.

13. The compound of claim 1 wherein for $R_1$ the radical $R_{11}$ is a substituted or unsubstituted heterocyclic radical selected from pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo(1,2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl or quinoxalinyl.

14. The compound of claim 1 in the form of a sodium salt.

15. The compound of claim 1 in the form of an ester prodrug.

16. A indole compound represented by the formula (II), or a pharmaceutically acceptable salt, solvate, or prodrug derivative thereof;

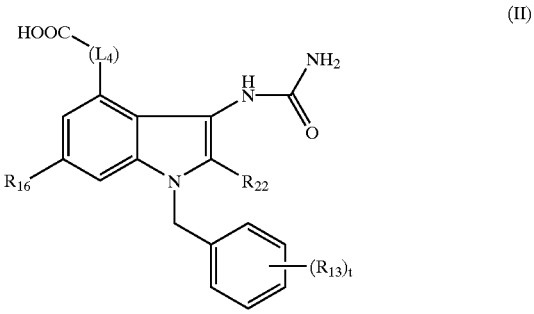

wherein;

$R_{16}$ is selected from hydrogen and $C_1$–$C_8$ alkyl, $C_1$–$C_8$ alkoxy, $C_1$–$C_8$ alkylthio $C_1$–$C_8$ haloalkyl, $C_1$–$C_8$ hydroxyalkyl, and halo;

—($L_4$)— is a divalent group selected from,

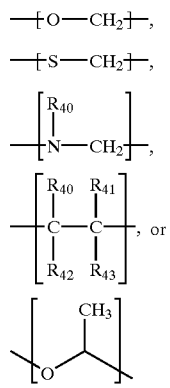

where $R_{40}$, $R_{41}$, $R_{42}$, and $R_{43}$ are each independently selected from hydrogen, $C_1$–$C_8$ alkyl;

$R_{22}$ is selected from hydrogen, methyl, ethyl, propyl, isopropyl, cyclopropyl, —F, —$CF_3$, —Cl, —Br, or —O—$CH_3$; and $R_{13}$ is $C_1$–$C_8$ alkyl, $C_1$–$C_8$ alkoxy, phenyl, halophenyl, —S—($C_1$–$C_8$ alkyl), $C_1$–$C_8$ haloalkyl, $C_1$–$C_8$ hydroxyalkyl, and halo; and t is an integer from 0 to 5.

17. A indole compound represented by the formula (C1);

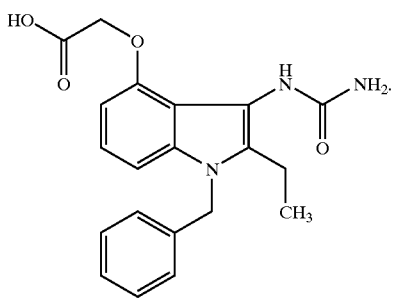

18. A pharmaceutical formulation comprising a indole compound as claimed in claim 1 together with a pharmaceutically acceptable carrier or diluent therefor.

19. A method of inhibiting sPLA$_2$ mediated release of fatty acid which comprises contacting sPLA$_2$ with an therapeutically effective amount of indole compound as claimed in claim 1.

20. A compound of claim 1 or a pharmaceutical formulation containing an effective amount of the compound of claim 1 in treatment of Inflammatory Diseases.

21. A compound of claim 1 or a pharmaceutical formulation containing an effective amount of the compound of claim 1 for use as an inhibitor for inhibiting sPLA$_2$ mediated release of fatty acid.

22. A compound of formula I in claim 1 for use in treatment of Inflammatory Diseases.

23. An indole compound represented by the formula (I), or a pharmaceutically acceptable salt, solvate, or prodrug derivative thereof;

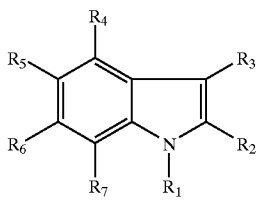

wherein;

$R_1$ is selected from groups (a), (b) and (c) wherein;
  (a) is $C_7$–$C_{20}$ alkyl, $C_7$–$C_{20}$ haloalkyl, $C_7$–$C_{20}$ alkenyl, $C_7$–$C_{20}$ alkynyl, carbocyclic radical, or heterocyclic radical, or
  (b) is a member of (a) substituted with one or more independently selected non-interfering substituents; or
  (d) is the group —(L$_1$)—R$_{11}$; where, —(L$_1$)— is a divalent linking group of 1 to 8 atoms and R$_{11}$ is a group selected from (a) or (b);

$R_2$ is hydrogen, or a group containing 1 to 4 non-hydrogen atoms;

$R_3$ is —(L$_3$)— Z, where —(L$_3$)— is a divalent linker group selected from a bond or a divalent group selected from:

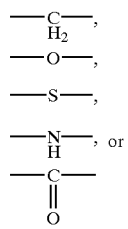

and Z is a ureido or thioureido group represented by the formulae,

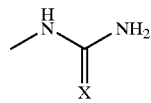

and X is oxygen or sulfur;

$R_4$ and $R_5$ each independently selected from hydrogen, a non-interfering substituent, or the group, —(L$_a$)-(acidic group), where —(L$_a$)—, is a divalent acid linker having an acid linker length of 1 to 8; provided that at least one of $R_4$ and $R_5$ must be the group, —(L$_a$)-(acidic group);

$R_6$ and $R_7$ are each independently selected from hydrogen, non-interfering substituent, carbocyclic radical, carbocyclic radical substituted with non-interfering substituent(s), heterocyclic radical, and heterocyclic radical substituted with non-interfering substituent(s).

* * * * *